(12) United States Patent
Pfeifer et al.

(10) Patent No.: US 8,296,078 B1
(45) Date of Patent: Oct. 23, 2012

(54) METHOD OF MULTI-DIMENSIONAL MOMENT ANALYSIS FOR THE CHARACTERIZATION OF SIGNAL PEAKS

(75) Inventors: Kent B. Pfeifer, Los Lunas, NM (US); William G. Yelton, Sandia Park, NM (US); Dayle R. Kerr, Sandia Park, NM (US); Francis A. Bouchier, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 790 days.

(21) Appl. No.: 12/491,733

(22) Filed: Jun. 25, 2009

(51) Int. Cl.
G01N 31/00 (2006.01)
G01N 30/02 (2006.01)
(52) U.S. Cl. .............. 702/24; 702/32; 73/23.37
(58) Field of Classification Search .......... 702/24, 702/32; 73/23.37
See application file for complete search history.

(56) References Cited

U.S. PATENT DOCUMENTS

| 4,353,242 A | * | 10/1982 | Harris et al. | 73/23.36 |
| 4,835,708 A | * | 5/1989 | Frans | 702/27 |
| 5,010,578 A | * | 4/1991 | Siener et al. | 382/108 |
| 2007/0143319 A1 | * | 6/2007 | Malek et al. | 707/101 |

* cited by examiner

*Primary Examiner* — Hezron E Williams
*Assistant Examiner* — Nathaniel Kolb
(74) *Attorney, Agent, or Firm* — Kevin W. Bieg

(57) ABSTRACT

A method of multi-dimensional moment analysis for the characterization of signal peaks can be used to optimize the operation of an analytical system. With a two-dimensional Péclet analysis, the quality and signal fidelity of peaks in a two-dimensional experimental space can be analyzed and scored. This method is particularly useful in determining optimum operational parameters for an analytical system which requires the automated analysis of large numbers of analyte data peaks. For example, the method can be used to optimize analytical systems including an ion mobility spectrometer that uses a temperature stepped desorption technique for the detection of explosive mixtures.

8 Claims, 6 Drawing Sheets

METHOD OF MULTI-DIMENSIONAL MOMENT ANALYSIS FOR THE CHARACTERIZATION OF SIGNAL PEAKS

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to the analysis of multi-component mixtures and, in particular, to a method of multi-dimensional moment analysis for the characterization of signal peaks that can be used to optimize the operation of an analytical system.

BACKGROUND OF THE INVENTION

Analysis of multi-component mixtures using various analytical techniques often results in data that can be represented as a signal that is a function of two or more dimensions (or variables). An example is gas chromatography coupled with ion mobility spectrometry (GC-IMS) where one dimension is ion drift-time ($t_d$) in the IMS and the other dimension is real-time elution ($t_r$) from the GC. Thus, the signal can be mathematically represented as $C(t_d, t_r)$. Such complexity has recently become relevant for IMS techniques that have responses in both the drift-time and the real-time dimensions.

A brief survey of the literature reveals a myriad of statistical two-dimensional techniques that have application for such data sets. Among these techniques are factor analysis techniques such as principle component analysis (PCA), evolving factor analysis (EFA), classical least-squares methods (CLS), inverse least-squares methods (ILS), and a number of techniques derived from these approaches (see A. de Juan and R. Tauler, *Journal of Chromatography A* 1158, 184 (2007); E. V. Thomas and D. M. Haaland, *Analytical Chemistry* 62(10), 1091 (1990); K. P. Pleibner et al., *Electrophoresis* 20, 755 (1999); D. M. Haaland and D. K. Melgaard, *Applied Spectroscopy* 54(9), 1303 (2000); and N. D. Sidiropoulos et al., *IEEE Transactions on Signal Processing* 48(8), 2377 (2000)). These approaches are generally designed to identify and quantify the concentration of a multi-component mixture measured using an analytical tool.

However, a need remains for a method to optimize the performance of an analytical system to provide a measurement with high quality and high fidelity. Accordingly, the present invention is directed to a method to quantify for comparison the quality and fidelity of signal response peaks. The method will be referred to herein as two-dimensional Péclet analysis.

SUMMARY OF THE INVENTION

The present invention is directed to a method of multi-dimensional moment analysis for the characterization of signal peaks, comprising measuring two or more signal peaks having at least two different dimensions of an analytical system; calculating a zero moment for each of the signal peaks; calculating a first moment in each dimension for each of the signal peaks; calculating a second moment in each dimension for each of the signal peaks; and selecting an operating parameter of the analytical system based upon a ratio of the first and second moments of each signal peak. The ratio can comprise a Péclet number. The operation of the analytical system can be optimized by selecting the operating parameter that corresponds to the signal peak having the highest Péclet number. The analytical system can comprise an ion mobility spectrometer with a preconcentrator in which the signal peak is a two-dimensional signal with drift time in the ion mobility spectrometer as a first dimension and real time desorption from that preconcentrator as a second dimension. Preferably, the preconcentrator enables temperature stepped desorption using two or more heating steps.

With a two-dimensional Péclet analysis, the quality and signal fidelity of peaks in a two-dimensional experimental space can be analyzed and scored. This method is particularly useful in determining optimum operational parameters for an analytical system which requires the automated analysis of large numbers of analyte data peaks. The technique is developed from moment analysis of the peaks and single dimensional Péclet theory. The two-dimensional Péclet analysis allows automated comparison of response peaks with differing shapes and amplitudes to be compared simultaneously in multicomponent mixtures. The method allows a direct, automated comparison between the quality of the peaks in-terms of peak shape and signal-to-noise ratio rather than to return a concentration and species analysis. It therefore provides a figure-of-merit in the form of a 2-D Péclet number that allows direct comparison of the signal fidelity of two or more peaks that have neither the same amplitude nor the same general shape and allows the system to be tuned to optimize its performance.

The method is applicable to any similar data occurring in a multi-dimensional space. The method can be used to optimize analytical systems, including an ion mobility spectrometer that uses a temperature stepped desorption technique for the detection of explosive mixtures as described herein. However, the method has more general applicability and can be used with the two-dimensional gel analysis in biological systems, "hyphenated" techniques such as gas chromatography coupled with mass spectrometry (GC-MS), time-frequency surface acoustic wave (SAW) tag data, geophysical analysis instruments for geophysical terrain mapping, navigation systems in mountainous areas, and effluent plume monitoring systems, for example.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

The method of the present invention is directed to a multidimensional moment analysis for the characterization of signal peaks, comprising measuring two or more signal peaks having at least two different dimensions of an analytical system; calculating a zero moment for each of the signal peaks; calculating a first moment in each dimension for each of the signal peaks; calculating a second moment in each dimension for each of the signal peaks; and selecting an operating parameter of the analytical system based upon a ratio of the first and second moments of each signal peak. The first moment is related to the distance from the origin of the peak. The second moment is related to the statistical variance or sharpness of the peak. The ratio can comprise a two-dimensional Péclet number; the ratio of the first moment squared divided by half the second moment squared.

The method of the present invention can be applied generally to the analysis of multi-component mixtures using various analytical techniques. However, the method will be described herein as applied to the characterization of signal peaks from an ion mobility spectrometer. Ion mobility spectroscopy is based on the atmospheric pressure ionization of a sample vapor and the subsequent separation of the individual ionized components, or analytes, of the sample mixture via electrophoresis as they are accelerated by an external electric field gradient and transit a time-of-flight drift tube against a neutral, counter-flowing gas stream. See G. A. Eiceman and Z. Karpas, *Ion Mobility Spectrometry*, $2^{nd}$ Ed., Chapter 4, (2004).

Figure 1:
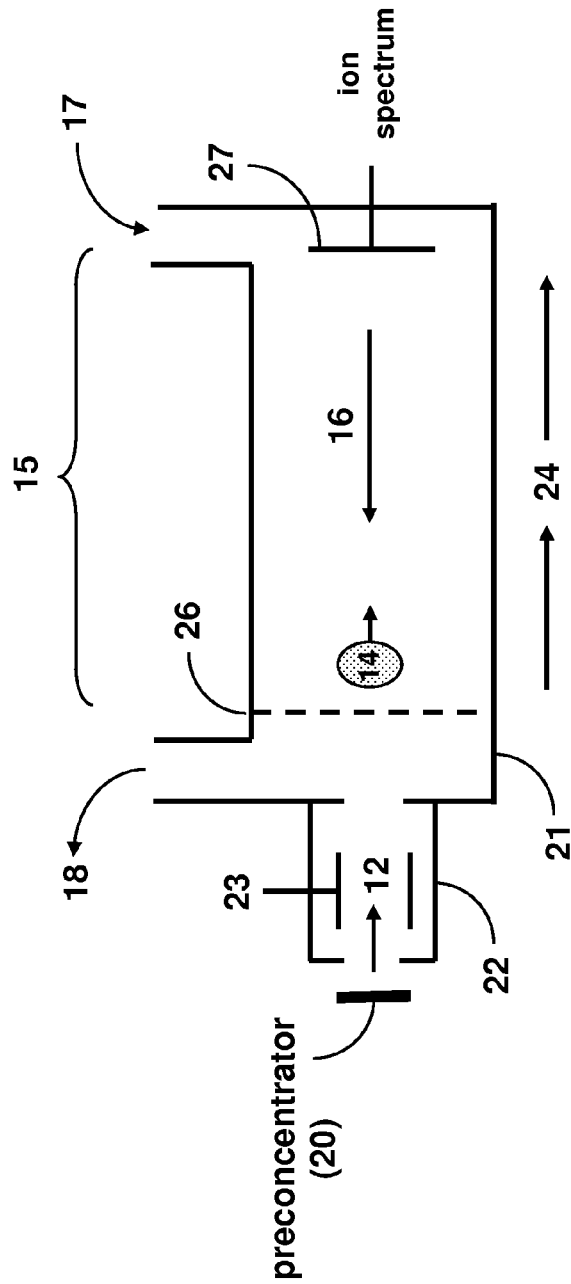
FIG. 1 is a schematic illustration of an ion mobility spectrometer (IMS) comprising a preconcentrator.

FIG. 1 shows a schematic illustration of an ion mobility spectrometer (IMS) 10 that uses a preconcentrator 20 to collect and concentrate analyte(s) of interest out of a large gas sample volume on a sorptive material at the inlet of the IMS. The preconcentrator 20 can deliver a sharp plug of analyte vapor to the downstream drift region 15 by rapid heating and release of the sorbed analyte. Alternatively, multiple sample pulses can be delivered using temperature stepped desorption (TSD) as described below. The analyte vapor 12 is drawn into an IMS drift tube 21 and ionized in an ionization region 22 (e.g., using a radioactive source, photoionization, or corona discharge ionizer 23), typically through proton transfer or electron capture reactions with reactant ions, to form product ions. A shutter grid 26 injects a pulse of ions 14 into the drift region 15 to begin a new measurement cycle. Drift gas is injected into the drift tube 21 via a drift gas inlet 17 and removed through a drift gas outlet 18. In the drift region 15, the ions establish a terminal velocity under the influence of the potential gradient of an electric field 24 and are separated into single ion swarms according to their characteristic ion mobility against the counter-flowing drift gas 16. The drift-induced separation begins at the shutter 26 and terminates at an ion collector 27 at the end of the drift region 15, where the ion response signal is recorded. For example, the ion collector 27 can comprise a collecting electrode or Faraday plate that records an ion response current. The drift-induced response of the IMS drift tube 21 is measured as a function of ion current versus the ion arrival time at the ion collector 27 for a measurement cycle. Compound identification is typically based on the comparison of the ion mobility spectrum generated from the sample with the spectra of known target analyte standards.

The drift-time of an explosive ion or any ion is a complex function of its ionization, mass, collision cross-section, and ion stability (see G. A. Eiceman and Z. Karpas, *Ion Mobility Spectrometry*, 2nd Ed., pp. 1-9 (2005)). Ions with different mobilities will reach a different terminal speed when an electric field is applied in the tube. Since there is a background gas in the tube, molecular collisions occur as the ion moves under the influence of the electric field resulting in a constant speed of the ion that is proportional to the electric field magnitude. The proportionality constant is known as the ion mobility and leads to separation in the transit time through the IMS drift tube.

Most IMS explosives detection systems that incorporate preconcentrators heat the preconcentrator to between 180° C. and 200° C. in a single pulse, which thermally desorbs the explosives that have been collected during sampling. This technique adequately desorbs the explosives; however, when multiple explosives are present in the sorbed sample, they are introduced into the IMS at the same time as a single sample plug with no real-time separation between them. By stepping the temperature of the preconcentrator up as a function of time, from below the boiling point of the most volatile of the analytes to above the boiling point of the least volatile analyte, the desorbed analytes can be separated as a function of time. Therefore, the use of a preconcentrator with temperature stepping enables real-time separation of analytes in a multicomponent mixture. The spectrum of ion arrival times at the ion collector is then a function of the desorption component of separation from the preconcentrator (i.e., real-time separation) and the relative ion mobility of each ion through the drift region (i.e., drift-time separation).

Figure 2:
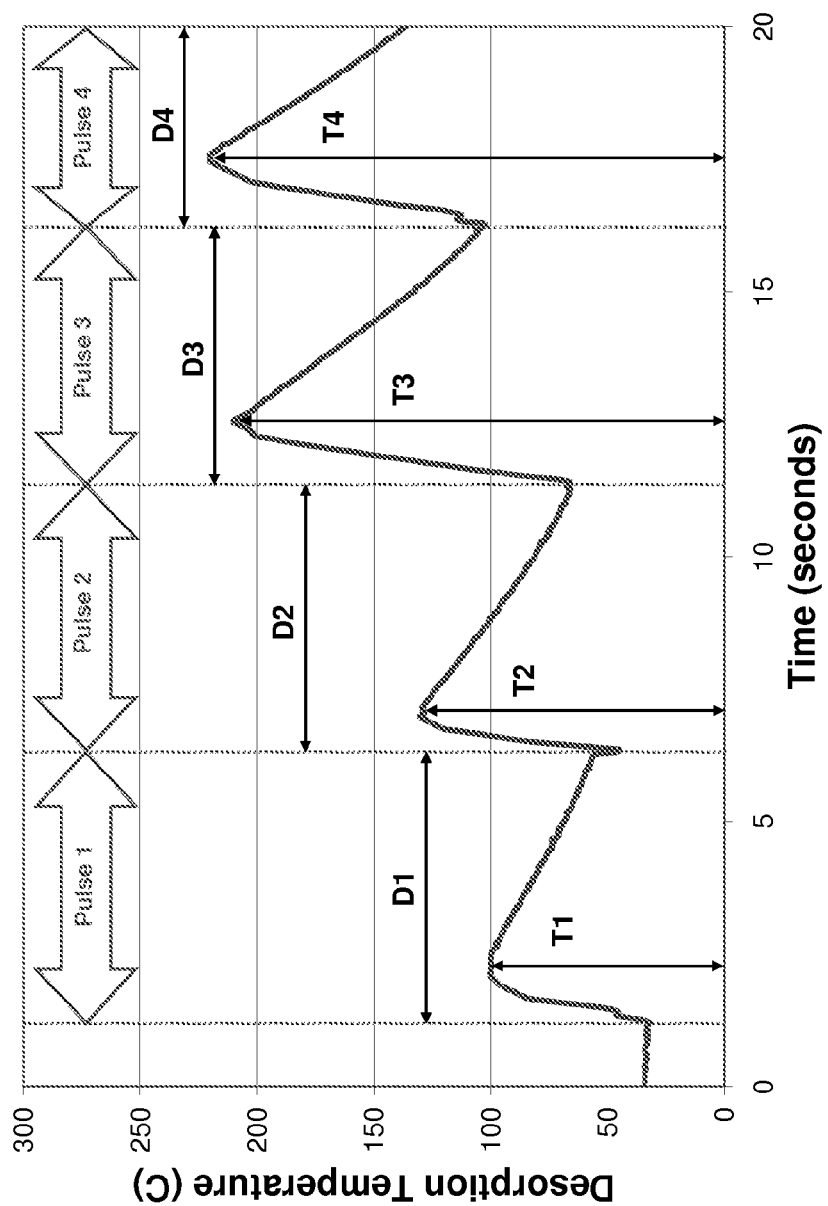
FIG. 2 is a graph of temperature stepped desorption comprising four heating steps.

As shown in FIG. 2, temperature stepped desorption (TSD) is a technique that pulses the preconcentrator with increasing heating steps. The four heating steps shown in this example raise the temperature starting at 100° C. and reach a final temperature of 220° C. Explosives with higher vapor pressures tend to desorb at the lower temperatures and explosives with lower vapor pressures often desorb at the higher temperatures. This technique is helpful for several reasons. TSD reduces the packet size of explosives entering the IMS at one time, which helps conserve the amount of reactant ion available to assist in the ionization process of the explosives and avoids saturating the detector, and separates the analytes in real time by heat of vaporization.

Separation in a real-time domain can be manipulated using TSD. With single thermal pulses, there is little separation in the real-time domain. However, if multiple thermal pulses exist, materials can be selectively desorbed into the IMS at varying temperatures, providing separation in the real-time domain. Therefore, TSD provides an additional dimension to differentiate between compounds when multiple component mixtures are present.

TSD is especially favorable to materials such as explosives that are thermally labile. Thermally labile compounds, such as pentaerythritol tetranitrate (PETN), will decompose at a high temperature between 180° C. and 200° C. TSD provides these explosives with the opportunity to desorb before the temperature reaches its decomposition point. Reduced decomposition will result in more effective detection and possibly improve the quantification ability of IMS for thermally labile compounds. Also, some explosives such as octahydro-1,3,5,7-tetranitro-1,3,5,7-tetrazocane (also known as HMX) do not thermally desorb from the preconcentrator until the temperature exceeds 200° C. With TSD, it is possible to detect mixtures containing PETN and HMX without significantly decomposing explosives such as PETN. In the past, this was not possible with a single, high-temperature pulse.

Multi-Dimensional Moment Analysis

A Péclet number in one dimension is defined, to first order, by the following equation for a plug flow experiment in a pipe.

$$Pe = \frac{2t^2}{\sigma^2} \quad (1)$$

If a plug of solute is injected into the pipe carrying a solvent at time zero and then measured at time t, the 1/e width of the plug, assuming a Gaussian distribution, is given as σ. Thus, the Péclet number provides a method of analysis of the spreading of the plug in the pipe due to diffusion, mixing, chemical reactions, and other spreading mechanisms (see R. Aris, *Chem. Eng. Sci.* 9, 266 (1959); and O. Levenspiel, *Chemical Reaction Engineering*, 2nd Edition, pp. 272-315, (1972)).

Figure 3:
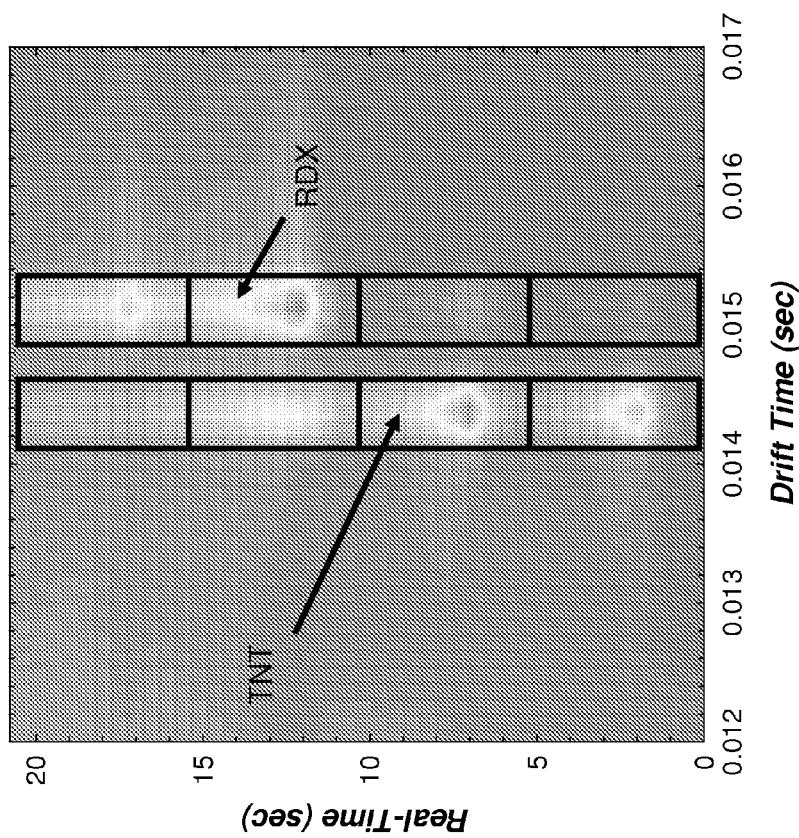
FIG. 3 is a representative data set illustrating the response of an IMS to RDX and TNT with the horizontal axis the IMS drift-time and the vertical axis the real-time.

FIG. 3 shows a representative data set that illustrates the two-dimensional nature with the real-time ($t_r$) data on the vertical axis representing the TSD component of separation from the preconcentrator and the horizontal axis representing the drift-time ($t_d$) in the IMS drift tube. Variation in grayscale represents the signal similar to a topographical map where the peaks are separated in real-time by the TSD and separated in drift-time by the IMS. The boxes are the data windows that are analyzed. A moment analysis can be performed on the data in each of the four windows individually. The general location of these windows is known a priori because of the nature of the experiment. The mobility of the target analyte standards is generally known, as well as when the preconcentrator is going to be heated to each temperature step. This defines the limits of the windows for integration. This aspect of the method represents a significant difference between the other statistical two-dimensional techniques mentioned above; their main purpose is to analyze an unknown peak to determine its species and quantity. This two-dimensional Péclet method of the present invention returns a figure-of-merit on a peak of known concentration and species, allowing comparison between measured peaks derived under different instrumental conditions. Thus, the instrumental conditions can be varied to optimize the known peaks of target analytes prior to analysis on unknown chemical compounds—in particular, multi-component mixtures.

By isolating an individual signal peak, as illustrated by the various windows in FIG. 3, the zero moment of the peak can be calculated from Eq. (2).

$$M_r^0 = M_d^0 = \int_{t_r=-\infty}^{t_r=\infty} \int_{t_d=-\infty}^{t_d=\infty} C(t_d, t_r) \, dt_d \, dt_r \quad (2)$$

where the zero moment of the distribution is proportional to the total mass of the detected analyte. The first moment in each dimension of the $C(t_d, t_r)$ data is the desorption peak location on the real- and drift-time axes and is found from Eq. (3).

$$M_r^1 = \bar{t}_r = \int_{t_r=-\infty}^{t_r=\infty} \int_{t_d=-\infty}^{t_d=\infty} \frac{t_r C(t_d, t_r)}{M_r^0} \, dt_d \, dt_r \quad (3)$$

$$M_d^1 = \bar{t}_r = \int_{t_r=-\infty}^{t_r=\infty} \int_{t_d=-\infty}^{t_d=\infty} \frac{t_d C(t_d, t_r)}{M_d^0} \, dt_d \, dt_r$$

The first moment is the centroid of the peak and represents the point on which the peak would balance on the point of a sharp object. The second moment, found from Eq. (4), is the variance of the peak in each dimension and quantifies the peak two-dimensional width ($\sigma_r^2$, $\sigma_d^2$).

$$M_r^2 = \sigma_r^2 = \int_{t_r=-\infty}^{t_r=\infty} \int_{t_d=-\infty}^{t_d=\infty} \frac{(\bar{t}-t_r)^2 C(t_d, t_r)}{M_r^0} \, dt_d \, dt_r \quad (4)$$

$$M_d^2 = \sigma_d^2 = \int_{t_r=-\infty}^{t_r=\infty} \int_{t_d=-\infty}^{t_d=\infty} \frac{(\bar{t}-t_d)^2 C(t_d, t_r)}{M_d^0} \, dt_d \, dt_r$$

This calculation relates the steepness of the peak and its ability to be separated from adjacent peaks. The second moment is also a good measure of signal fidelity and resolution in the analytical system.

The moment analysis can be done in each individual data window by calculating the "zero" moment of the peak, according to Eq. (2). Here, the units are volts·sec$^2$, representing the concentration multiplied by the time variables (see L. Leithold, *The Calculus with Analytic Geometry*, 4$^{th}$ ed, pp. 595-609 (1981)). The centroid of the peak in two dimensions can then be calculated, according to Eq. (3). This is mathematically equivalent to determining the point of balance of a peak or first moment in the contour map analogy for each of the dimensions where $\bar{t}_d$ and $\bar{t}_r$ are the first moments represented as time-domains for the peak. Next, the peak width can be determined by calculating the second moment in both dimensions, according to Eq. (4). This is equivalent to determining the standard deviation of the peak (see L. C. Andrews and R. L. Phillips, *Mathematical Techniques for Engineers and Scientists*, pp. 650-651 (2003)).

Figure 4:
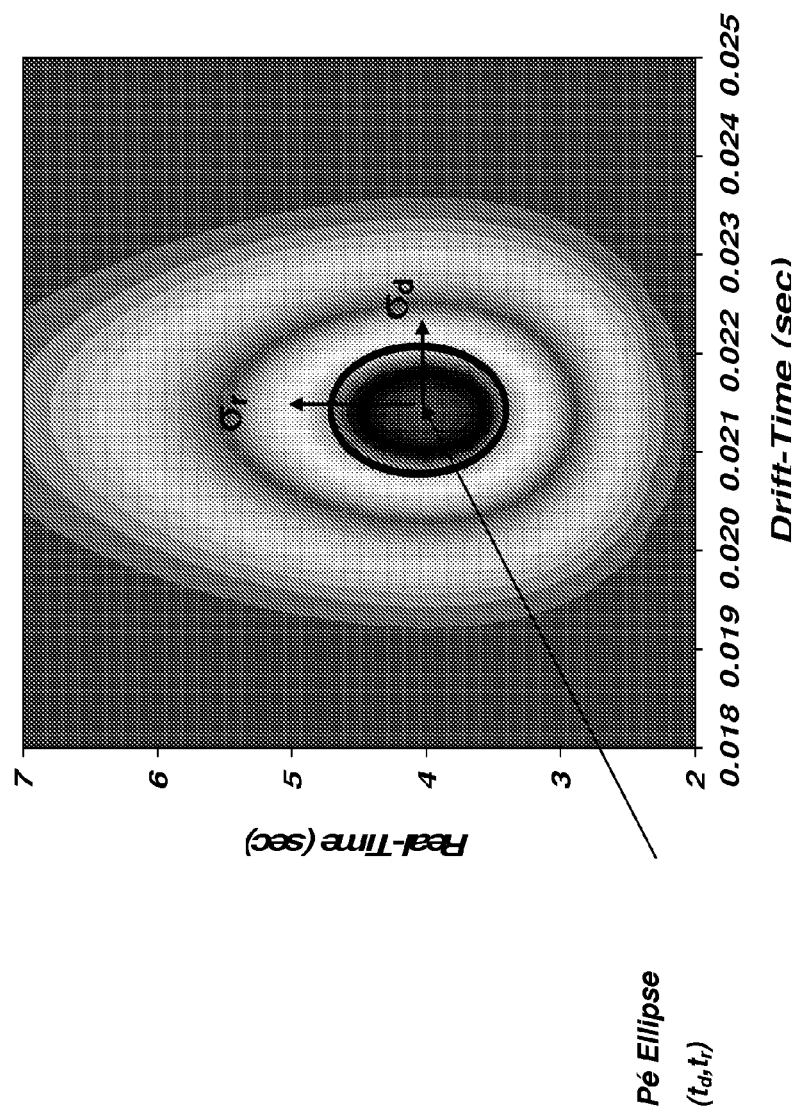
FIG. 4 is a plot illustrating the relationships of the two-dimensional first moment (centroid) and second moment (standard deviation) for an IMS peak drawn as a contour plot. The centroid of the peak is located at the coordinate ($t_d, t_r$) and has a standard deviation in its x-position of $\sigma_d$ and its y-position of $\sigma_r$.

If the location of the peak is defined as a vector where $\vec{t} = \bar{t}_d \hat{i} + \bar{t}_r \hat{j}$ is the centroid of the peak in time space, where $\bar{t}_d$ is the average drift time and $\bar{t}_r$ is the average real-time of the first moments in both dimensions, and $\vec{\sigma} = \sigma_d \hat{i} + \sigma_r \hat{j}$, where $\sigma_d$ and $\sigma_r$ are the standard deviation (second moment) for both real-time and drift time domains, (the symbols $\hat{i}$ and $\hat{j}$ denote unit vectors in the x- and y-dimension respectively), then an ellipse at the 1/e point of the two-dimensional peak can be fitted. FIG. 4 is a plot illustrating the relationships of the two-dimensional first moment (centroid) and second moment (standard deviation) for an IMS peak drawn as a contour plot. The centroid of the peak is located at the coordinate ($t_d, t_r$) and has a standard deviation in its x-position of $\sigma_d$ and its y-position of $\sigma_r$.

The Péclet number for the individual peak is calculated by geometrically adding the ratio of the variance to the mean, assuming uncorrelated spreading, to get the total standard deviation, $$\sigma^2 = \left(\frac{\sigma_d^2}{\bar{t}_d^2} + \frac{\sigma_r^2}{\bar{t}_r^2}\right)(\bar{t}_d^2 + \bar{t}_r^2) \quad (5)$$

and substituting into Eq. (1) to obtain the following:

$$Pe = 2\left(\frac{\bar{t}_d^2 \bar{t}_r^2}{\sigma_r^2 \bar{t}_d^2 + \sigma_d^2 \bar{t}_r^2}\right) \quad (6)$$

In an ideal system, the Péclet number is a measure of the ratio of the rate of analyte transport divided by the rate of spreading (see H. Scott Fogler, *Elements of Chemical Reac-* tion Engineering, 2nd edition, p. 767 (1992)). In practice, a planar preconcentrator or any practical preconcentrator/separator has a peak width determined not only by diffusion of the analyte following desorption, but also by desorption, heating rate, distribution of desorption energy from binding sites on the absorbent bed, temperature gradients across the absorber, and other factors. This is represented by the value of $\sigma_r$. The width of the detected peak ($\sigma_d$) in IMS is a function of several distinct phenomena that are time dependent. Namely, these are the initial pulse width, diffusion (dependent on gas temperature and transit time), electrostatic space charge effects, capacitive coupling between approaching ions and the collector, electric-field gradients, temperature gradients, gate depletion/dynamic leakage, pressure fluctuations, and ion-molecule reactions in the drift space (see J. Xu et al., *Analytical Chem.* 72(23) 5787 (2000); K. B. Pfeifer and R. C. Sanchez, *Int. Journal for IMS* 5(3), 63 (2002); and K. B. Pfeifer and A. N. Rumpf, *Anal. Chem.* 77(16) 5215 (2005)).

The calculated moments and Péclet values provide a quantitative comparison of system performance under different sets of operating conditions, but cannot be interpreted as due only to contributions of convective and diffusive transport.

Figure 5:
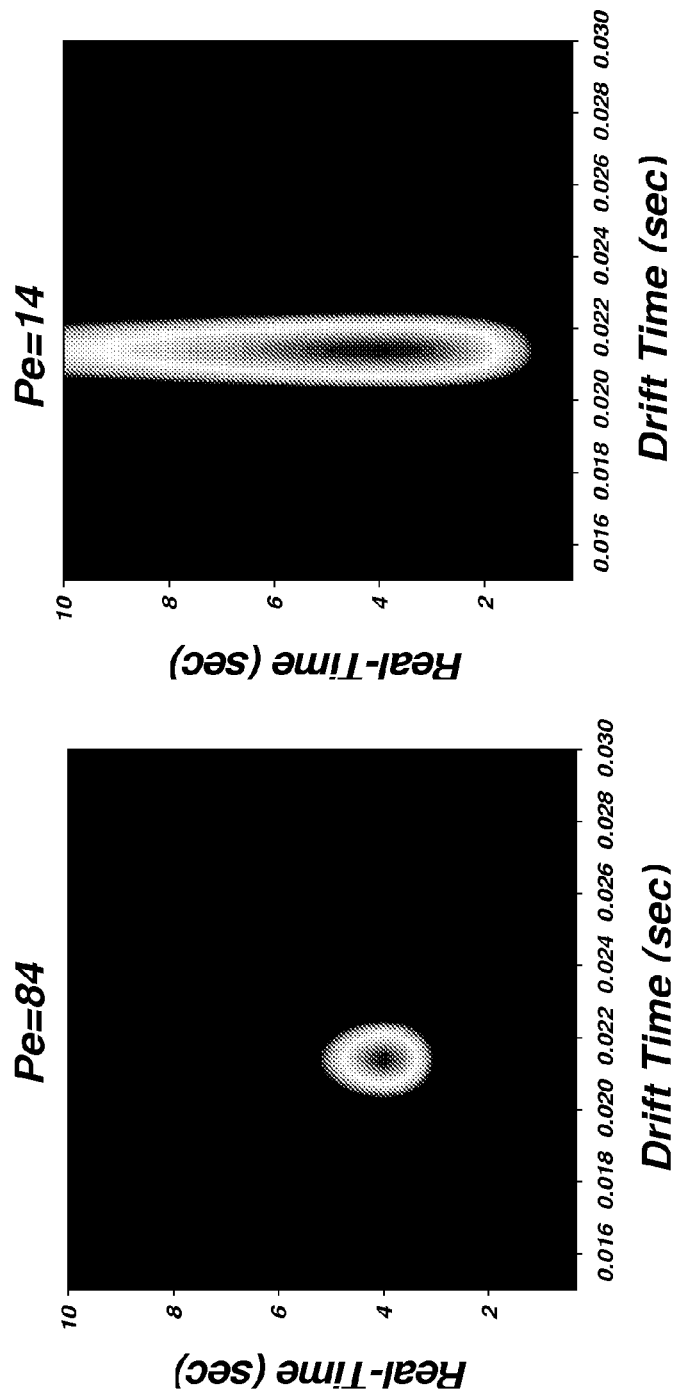
FIG. 5 shows two different data peak shapes representing IMS results with no variation in the drift width that are allowed to expand in the real-time domain as the elution peak widths are increased. The corresponding Péclet number is shown with each peak.

FIG. 5 shows plots of two peak shapes and their corresponding Péclet numbers. Both peaks have the same amplitude but different real-time spread, resulting in different volumes. However, note that volume is normalized out of the first and second moment calculation in Eqs. (3) and (4). Thus, the Péclet number is significantly higher for the more distinct peak (84) than for the more diffuse peak (14). This analysis can be used to automate scoring and comparison of different response peaks to gain insight into resolvability and signal fidelity of the IMS. In a practical system where peaks are close together or over-lapped, the algorithm will score the peak with a lower Péclet number because the peak will not be sharp and the value of the second moment will be larger in Eq. (4) causing the value of the Péclet number (Eq. (6)) to be smaller. Similarly, a highly resolved peak will have a large Péclet number since its second moment will be smaller.

Experimental Results

A series of experiments were conducted to optimize the separation and detection of RDX and 2-methyl-1,3,5-trinitrobenzene (TNT) explosives using an IMS coupled with a preconcentrator operating in the TSD mode. A total of 1028 different runs, with 21 distinct concentration profiles and 48 distinct temperature profiles, provided over 8000 separate signal peaks. The system consisted of a preconcentrator, comprising a stainless steel felt that could be electrically heated, coupled to a PCP IMS operating as a detector. In actual application, large volumes of room air that potentially contain particles of explosives are drawn through the felt and then desorbed by heating into the IMS input. In this experiment, in order to maintain consistency, dissolved samples of explosives were deposited using a micro-liter syringe onto the center of the felt and then heated to desorb them. After the limiting ranges were chosen, a Hardin-Sloane I-optimal design was used to determine sets of values of the operating parameters for which experimental measurements were made (see R. H. Hardin and N. J. A. Sloane, *Journal of Statistical Planning and Inference* 37(3), 339 (1993)). The run order for the parameter sets was randomized to minimize systematic bias due to unknown factors.

Figure 6:
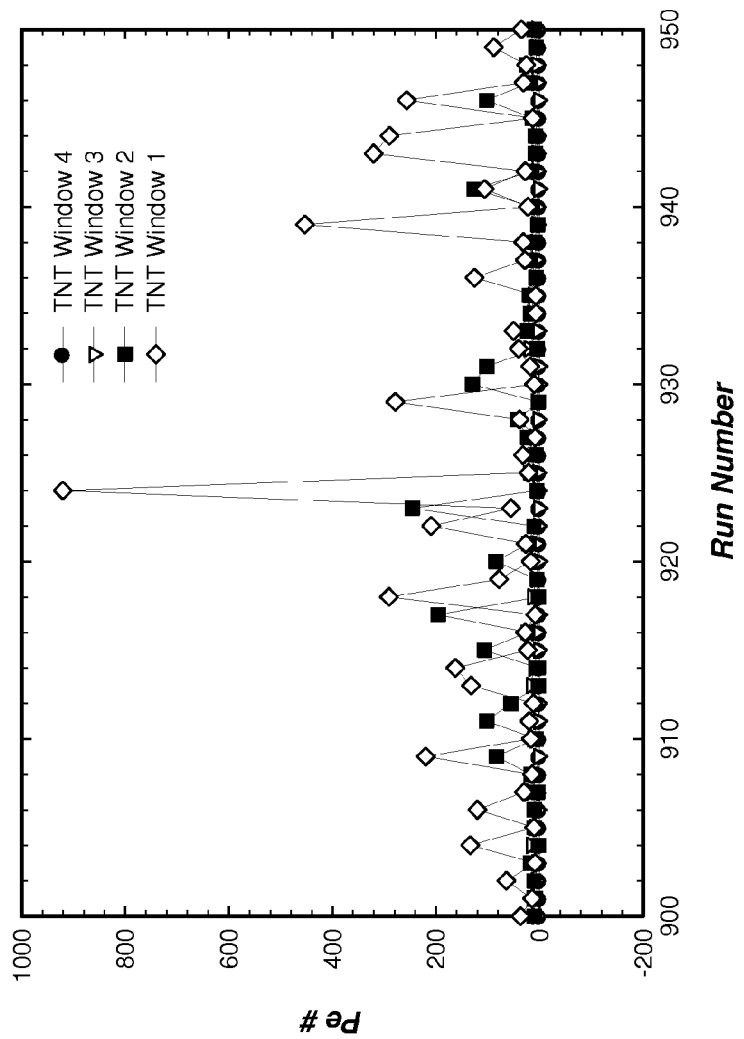
FIG. 6 is a plot of subset of "recipe" number vs. Péclet number illustrating the optimization of the time-delay and temperature steps for measuring 2-methyl-1,3,5-trinitrobenzene (TNT) using a preconcentrator and IMS.

A subset of the data is shown in FIG. 6, which illustrates the application of the Péclet technique. This plot shows a subset of "recipe" number (i.e., run number) vs. Péclet number illustrating the optimization of the time-delay and temperature steps for measuring TNT using the preconcentrator and IMS. The Péclet number for experiment number 924 for TNT is much larger for window 1 than for windows 2-4. In addition, other tests with different delay times and temperature steps do not produce the high Péclet number. Thus, the "recipe" represented by run 924 is optimized to produce a high fidelity TNT peak for this IMS measurement system. By employing this two-dimensional Péclet method, the peaks can be automatically scored and the operational parameters of the IMS system can thus be optimized.

The present invention has been described as a method of multi-dimensional moment analysis for the characterization of signal peaks. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method of multi-dimensional moment analysis for the characterization of signal peaks, comprising:
    measuring two or more signal peaks having at least two different dimensions of an analytical system comprising an ion mobility spectrometer with a preconcentrator;
    calculating a zero moment for each of the signal peaks;
    calculating a first moment in each dimension for each of the signal peaks;
    calculating a second moment in each dimension for each of the signal peaks; and
    selecting an operating parameter of the analytical system based upon a ratio of the first and second moments of each signal peak wherein each signal peak is a two-dimensional signal peak with the first dimension comprising the drift time in the ion mobility spectrometer and the second dimension comprising the real time desorption from the preconcentrator.

2. The method of claim 1, wherein the real time desorption comprises temperature stepped desorption from two or more heating steps of the preconcentrator.

3. The method of claim 1, wherein the ion mobility spectrometer further comprises a gas chromatograph.

4. The method of claim 1, wherein each signal peak is a two-dimensional signal peak and the zero moment is calculated according to $$M_r^0 = M_d^0 = \int_{t_r=-\infty}^{t_r=\infty} \int_{t_d=-\infty}^{t_d=\infty} C(t_d, t_r) \, dt_d \, dt_r,$$

where C is the signal as a function of a first dimension $t_d$ and a second dimension $t_r$.

5. The method of claim 4, wherein the first moments are calculated according to $$M_r^1 = \bar{t}_r = \int_{t_r=-\infty}^{t_r=\infty} \int_{t_d=-\infty}^{t_d=\infty} \frac{t_r C(t_d, t_r)}{M_r^0} \, dt_d \, dt_r$$

$$M_d^1 = \bar{t}_r = \int_{t_r=-\infty}^{t_r=\infty} \int_{t_d=-\infty}^{t_d=\infty} \frac{t_d C(t_d, t_r)}{M_d^0} \, dt_d \, dt_r.$$

6. The method of claim 5, wherein the second moments are calculated according to $$M_r^2 = \sigma_r^2 = \int_{t_r=-\infty}^{t_r=\infty} \int_{t_d=-\infty}^{t_d=\infty} \frac{(\bar{t}-t_r)^2 C(t_d, t_r)}{M_r^0} dt_d\, dt_r$$

$$M_d^2 = \sigma_d^2 = \int_{t_r=-\infty}^{t_r=\infty} \int_{t_d=-\infty}^{t_d=\infty} \frac{(\bar{t}-t_d)^2 C(t_d, t_r)}{M_d^0} dt_d\, dt_r.$$

7. The method of claim 6, wherein the ratio of the first and second moments comprises a Péclet number that is calculated according to $$Pe = 2\left(\frac{\bar{t}_d^2 \bar{t}_r^2}{\sigma_r^2 \bar{t}_d^2 + \sigma_d^2 \bar{t}_r^2}\right).$$

8. The method of claim 7, wherein the step of selecting comprises selecting the operating parameter of the analytical system corresponding to the signal peak having the highest Péclet number.

* * * * *